(12) United States Patent
Nishimura et al.

(10) Patent No.: US 9,120,842 B2
(45) Date of Patent: Sep. 1, 2015

(54) SPARC-DERIVED TUMOR REJECTION ANTIGENIC PEPTIDES AND MEDICAMENTS COMPRISING THE SAME

(71) Applicant: ONCO THERAPY SCIENCE, INC., Kanagawa (JP)

(72) Inventors: Yasuharu Nishimura, Kumamoto (JP); Yoshiaki Ikuta, Kumamoto (JP); Shuichi Nakatsuru, Kanagawa (JP)

(73) Assignee: ONCO THERAPY SCIENCE, INC., Kanagawa (JP)

( * ) Notice: Subject to any disclaimer, the term of this patent is extended or adjusted under 35 U.S.C. 154(b) by 189 days.

(21) Appl. No.: 13/901,194

(22) Filed: May 23, 2013

(65) Prior Publication Data
US 2013/0288363 A1    Oct. 31, 2013

Related U.S. Application Data

(62) Division of application No. 13/243,259, filed on Sep. 23, 2011, now Pat. No. 8,470,968, which is a division of application No. 12/304,350, filed as application No. PCT/JP2007/062117 on Jun. 15, 2007, now Pat. No. 8,053,557.

(30) Foreign Application Priority Data

Jun. 16, 2006   (JP) ................................. 2006-167724

(51) Int. Cl.
| | | |
|---|---|---|
| C07K 7/06 | (2006.01) | |
| A61K 39/00 | (2006.01) | |
| C07K 14/47 | (2006.01) | |
| C07K 16/18 | (2006.01) | |
| A61K 38/00 | (2006.01) | |

(52) U.S. Cl.
CPC ............... *C07K 7/06* (2013.01); *A61K 39/0011* (2013.01); *C07K 14/47* (2013.01); *C07K 16/18* (2013.01); *A61K 38/00* (2013.01); *A61K 2039/5154* (2013.01)

(58) Field of Classification Search
None
See application file for complete search history.

(56) References Cited

U.S. PATENT DOCUMENTS

| | | |
|---|---|---|
| 6,794,363 B2 | 9/2004 | Bejanin et al. |
| 7,005,500 B2 | 2/2006 | Bejanin et al. |
| 7,030,222 B2 | 4/2006 | Kikuchi et al. |
| 8,053,556 B2 | 11/2011 | Nishimura et al. |
| 8,053,557 B2 | 11/2011 | Nishimura et al. |
| 8,470,968 B2 | 6/2013 | Nishimura et al. |
| 2006/0204960 A1 | 9/2006 | Nakamura et al. |
| 2006/0251666 A1 | 11/2006 | Nakatsura et al. |
| 2008/0044818 A1 | 2/2008 | Nishimura et al. |
| 2009/0074800 A1 | 3/2009 | Nakatsura et al. |
| 2009/0111095 A1 | 4/2009 | Nishimura et al. |

FOREIGN PATENT DOCUMENTS

| | | |
|---|---|---|
| EP | 1 813 943 | 8/2007 |
| JP | 2004-303688 | 10/2004 |
| JP | 2006-503575 | 2/2006 |
| WO | 02/00677 | 1/2002 |
| WO | 2004/038045 | 5/2004 |
| WO | 2006/043362 | 4/2006 |

OTHER PUBLICATIONS

Nakatsura, T. et al., Clin. Cancer Res., 2004, vol. 10, No. 24, pp. 8630-8640.
Wang, C.S. et al., Br. J. Cancer, 2004, vol. 91, No. 11, pp. 1924-1930.
Ikuta, Y. et al., Clin. Cancer Res., 2005, vol. 11, No. 22, pp. 8079-8088.
Komori, H. et al., Clin. Cancer Res., 2006, vol. 12, No. 9, pp. 2689-2697.
Akiyama, H. et al., Immunol. Letters, 2002, vol. 83, No. 1, pp. 21-30.
Ikuta, Y. et al., "Gan Kogen SPARC o Mochiita Gan Men'eki Ryoho Model no Kakuritsu", Dai 10 Kai Society for Fundamental Cancer Immunology Sokai Shoroku, Jun. 30, 2006, p. 58, along with an English language translation thereof.
Ikuta, Y. et al., "Gan Tokuiteki ni Kohatsugen suru SPARC o Hyoteki to shita Mouse Gan Men-eki Ryoho Model no Kochiku", Dai 65 Kai Annual Meeting of the Japan Cancer Association Kiji, Aug. 28, 2006, p. 62 [0-147], along with an English language translation thereof.
Kohler, G. et al., Nature, 1975, vol. 256, No. 551, pp. 495-497.
Takahashi, H. et al. Nature, 1990, vol. 344, No. 6269, pp. 873-875.
Mouritsen S. et al., J. Immunol., 1992, vol. 148, No. 5, pp. 1438-1444.
Ikuta et al., "Identification of the $H2\text{-}K^d$-restricted Cytotoxic T Lymphocyte Epitopes of a Tumor-associated Antigen, SPARC, which can Stimulate Antitumor Immunity without Causing Autoimmune Disease in Mice" *Cancer Sci.* 100(1):132-137, 2009.
Sangaletti et al., "Leukocyte, Rather than Tumor-produced SPARC, Determines Stroma and Collagen Type IV Deposition in Mammary Carcinoma" *J. Exp. Med.* 198(10):1475-1485, 2003.
Guweidhi et al., "Osteonectin Influences Growth and Invasion of Pancreatic Cancer Cells" *Ann. Surg.* 242(2):224-234, 2005.
Jones (Pharmacogenomics Journal, 1:126-134, 2011).

(Continued)

*Primary Examiner* — Brad Duffy
(74) *Attorney, Agent, or Firm* — Greenblum & Bernstein, P.L.C.

(57) ABSTRACT

It is an objective of the present invention to identify SPARC protein-derived peptides that are able to induce human killer T cells and helper T cells having cytotoxic activity to tumors, and to provide a means for carrying out a tumor immunotherapy of patients with various types of cancers overexpressing SPARC. The present invention provides a peptide of any of the following:

(A) a peptide which consists of the amino acid sequence as shown in any one of SEQ ID NOS: 1 to 3; or
(B) a peptide which consists of an amino acid sequence comprising a substitution or addition of one or several amino acids with respect to the peptide consisting of the amino acid sequence as shown in any one of SEQ ID NOS: 1 to 3, and which has capacity to induce cytotoxic (killer) T cells.

3 Claims, 4 Drawing Sheets

(56) References Cited

OTHER PUBLICATIONS

Tosatto et al (Current Pharmaceutical Design, 12:2067-2086, 2006).
Elgert et al (Immunology: Understanding the Immune System, 1996, pp. 143-145).
Skolnick et al. (Trends in Biotechnology 2000; 18: 34-39).
Bowie et al. (Science 257: 1306-1310, 1990).
DeGruijl T.D. et al (Nature Medicine, 5(10): 1124-1125, Oct. 1999).
Wang et al. (Exp. Opin. Biol. Ther. 2001; 1 (2): 277-290).
Bodey et al. (Anticancer Research. 2000; 20:2665-2676).
Boon (Advances in Cancer Research. 1992; 58:177-210).
Arceci (Journal of Molecular Medicine. 1998; 76: 80-93).
U.S. Appl. No. 13/242,019 to Yasuharu Nishimura et al., which was filed on Sep. 23, 2011.
Office Action for Chinese Patent Application No. 201310236439.X, dated Aug. 5, 2014, along with an English language translation.
Indian Office Action issued with respect to Indian Patent Application No. 252/CHENP/2009, dated Feb. 18, 2014.
Office Action for Chinese Patent Application No. 201310236439.X, dated Apr. 21, 2015, along with an English language translation.

Identification of mouse Kd (≒HLA-A24)-rescricted SPARC epitope peptide in de in BALB/c mouse, and damage of SPARC-positive tumor cells by induced CTL Growth inhibition and extension of survival time of Meth A cancer cells by pre-administration of bone marrow-derived dendric cells (BM-DC) which were loaded with a mixture of SPARC Kd-1, 3 and 4 peptides to BALB/c mouse

SPARC-DERIVED TUMOR REJECTION ANTIGENIC PEPTIDES AND MEDICAMENTS COMPRISING THE SAME

CROSS-REFERENCE TO RELATED APPLICATIONS

This application is a Divisional of U.S. patent application Ser. No. 13/243,259, filed Sep. 23, 2011, which is a Divisional of U.S. patent application Ser. No. 12/304,350 (now U.S. Pat. No. 8,053,557), which is the National Stage of International Application No. PCT/JP2007/062117, filed Jun. 15, 2007. The entire disclosures of each of the above-cited applications are considered as being part of this application and are expressly incorporated herein by reference in their entireties. This application also claims priority to Japanese Patent Application No. JP 2006-167724, filed Jun. 16, 2006.

TECHNICAL FIELD

The present invention relates to novel peptides that are effective as a vaccine for cancers highly expressing SPARC, such as stomach cancer, pancreatic cancer or malignant melanoma (melanoma), and medicaments comprising the aforementioned peptides used for treating and/or preventing tumors.

BACKGROUND ART

When compared with Western countries, the morbidity of stomach cancer is high in Asian countries such as Japan and China. As a result of diffusion of medical check-ups, the widespread use of digestive endoscopes, and the development of inspection techniques, it has become possible to detect stomach cancer at an early stage, and thus the number of patients suffering from this cancer has been decreasing. Nevertheless, stomach cancer is still the second cause of death due to malignant neoplasm in the Japanese population. Thus, stomach cancer is still a main cause of death. Among several types of stomach cancers, diffuse (scirrhous) stomach cancer occurs in young people when compared with another type of stomach cancer (adenocarcinoma). Such diffuse (scirrhous) stomach cancer tends to make rapid progress, and distant metastasis or peritoneal metastasis frequently occurs, thereby resulting in poor prognosis. In many cases of scirrhous stomach cancer, it has already become impossible to carry out surgical excision at the time of diagnosis. Even if it is still possible to excise the tumor, the cancer often recurs after the treatment. Accordingly, it is highly desired to establish a novel treatment method.

The death toll from pancreatic cancer tends to increase in Japan. 21,148 people died due to pancreatic cancer in 2003. At present, such pancreatic cancer makes up 6.8% of the cancers that cause death in Japan. That is, pancreatic cancer ranks fifth cause of death after lung cancer, stomach cancer, colon cancer, and liver cancer. The world demographic data was analyzed, and the age-adjusted mortality rate, which is used for comparison among the mortality rates of populations with different age structures, was calculated. As a result, in 2000, in the case of 100,000 males, 8.6 people died due to pancreatic cancer in Japan, whereas 7.3 people died in the United States and 6.3 to 7.0 people died in the United Kingdom due to the same type of cancer. In the case of 100,000 females, 4.9 people died due to pancreatic cancer in Japan, whereas 5.3 people died in the United States and 4.8 to 5.1 people died in the United Kingdom due to the same type of cancer. Thus, the mortality rate due to pancreatic cancer in Japan has become the same level as those of Western countries.

Taking into consideration the age-adjusted rate in 2000 (100,000 people of the world's population), in the case of males, 8.6 people died due to pancreatic cancer in Japan, whereas 7.3 people died in the United States and 6.3 to 7.0 people died in the United Kingdom due to the same type of cancer. In addition, in the case of females, 4.9 people died due to pancreatic cancer in Japan, whereas 5.3 people died in the United States and 4.8 to 5.1 people died in the United Kingdom due to the same type of cancer. Thus, the mortality rate due to pancreatic cancer in Japan has become the same level as those of Western countries. In spite of the development of diagnostic imaging, at present, approximately 40% of the total Japanese patients with pancreatic cancer suffer from progressive pancreatic cancer involving distant metastasis, and further, there are also many cases where the cancer is discovered after it has reached a locally-advanced cancer stage, at which tumor cannot be excised. The 5-year relative survival rate of total patients with pancreatic cancer is 4.3% in the diagnosis cases in 1996. Although this rate tends to be higher than the conventional survival rate (2% to 3%), it is still low. Regarding factors of developing pancreatic cancer, it has been suggested that various factors including life habit such as smoking, adiposis, meals, alcohol drinking, and coffee use, as well as chronic pancreatitis, diabetes, genetic factor, etc. are involved in the onset of pancreatic cancer.

Pancreatic cancer does not have specific symptoms, and thus, in many cases, the cancer has already progressed when certain symptoms appear. As a result, the 5-year survival rate of total patients is 5% or less, and prognosis after the diagnosis is extremely low. Due to difficulty in the diagnosis of pancreatic cancer, the rate of this cancer as a causative disease of cancer death is gradually increased particularly in advanced countries. Currently, multidisciplinary therapy including a surgical excision as a main treatment, a radiotherapy, and a chemotherapy, has been carried out. However, no drastic improvement of therapeutic effects can be obtained, and thus, the establishment of a novel therapeutic strategy is urgently necessary.

Melanoma is one type of skin cancer, which is often called malignant melanoma. Among several types of skin cancers, melanoma is highly likely to become infiltrative and metastatic and has the highest grade of malignancy, and thus it is greatly feared. Among cells that constitute skin, several cells generate melanin pigment. Such cells are called melanocytes. When such melanocytes become cancerous, melanoma occurs. In addition, the frequency of occurrence of melanoma has been increasing, particularly among Caucasians, as a result of an increase in exposure to ultraviolet rays due to a reduction in the ozone layer in the atmosphere caused by environmental destruction.

In Japan, the incidence of melanoma varies from 1.5 to 2 people in 100,000 in the general population. Thus, it is estimated that approximately 1,500 to 2,000 people develop melanoma per year. On the other hand, in the Western countries, more than a dozen of people develop melanoma in 100,000 in the general population. In particular, in Australia, twenty or more people develop such melanoma in 100,000 in the general population, and thus it is known that the incidence of melanoma in Australia is the highest in the world. Under such circumstances, people who live in Europe, the United States, and Australia are interested in melanoma, and they pay attention to the occurrence of melanoma. Furthermore, surprisingly, the occurrence of melanoma tends to be increasing year after year in Japan as well as in foreign countries.

According to recent studies, the annual death toll from melanoma is approximately 450 in Japan. Melanoma develops regardless of age. However, the incidence of this disease increases for those over 40, and it is the highest for those in their 60's and 70's. The onset of this disease in childhood is extremely rare, but this does not mean that the disease never develops in childhood. Recently, the occurrence of melanoma tends to be increasing in young patients in their 20's and 30's. Melanoma develops regardless of sex, and both male and female patients suffer from this disease. In the case of Japanese patients, the site at which melanoma is most likely to develop is the sole (the sole of the foot), and it accounts for 30% of all instances of melanoma. As characteristics of Japanese patients, melanoma also develops in the foot and the nail portions of the fingers. In addition, as in the case of Western patients, melanoma develops in all parts of the skin, such as the body, hand, foot, face, and head.

At present, methods that can be applied to treat melanoma include a surgical therapy, a chemotherapy, and a radiotherapy. However, as a therapy for alleviating the symptoms of metastatic cancer or intractable cancer, to which the aforementioned therapy cannot be applied, an immunotherapy for enhancing the immunity of a cancer patient to cancer so as to suppress the growth of the cancer has become a focus of attention. Such an immunotherapy is actually effective for some patients.

On the other hand, with the development of molecular biology and tumor immunology in recent years, it has been revealed that cytotoxic (killer) T cells and helper T cells recognize peptides generated by degradation of proteins highly and specifically expressed in cancer cells, which are presented on the surfaces of the cancer cells or antigen-presenting cells via HLA molecules, and that they exhibit an immune reaction for destroying such cancer cells. Moreover, a large number of tumor antigenic proteins and peptides derived from them, which stimulate such an immune reaction for attacking cancers, have been identified, and clinical application of an antigen-specific tumor immunotherapy has been advanced.

HLA class I molecules are expressed on the surfaces of all nucleated cells in a body. Proteins generated in cytoplasms and nuclei provide peptides generated as a result of being degraded in cells, and they are expressed on the surfaces of such cells. On the surfaces of normal cells, peptides derived from normal autologous proteins bind to HLA class I molecules, and T cells of the immune system neither recognize nor destroy such peptides bound to HLA class I molecules. On the other hand, in a process in which cancer cells are converted to a cancer, such cancer cells may express large amounts of proteins, which are hardly expressed or are only expressed in small amounts on normal cells. If a peptide generated by degradation in the cytoplasm of such a protein that is highly expressed specifically in a cancer cell binds to an HLA class I molecule and is expressed on the surface of such a cancer cell, a killer T cell recognizes the peptide and destroys only the cancer cell. In addition, by immunizing such a cancer-specific antigen or peptide to an individual body, it is possible to destroy cancer cells and suppress the growth of a cancer, without impairing normal cells. This is referred to as cancer immunotherapy using a cancer-specific antigen. Moreover, an HLA class II molecule is mainly expressed on the surface of an antigen-presenting cell. Such an HLA class II molecule binds peptides derived from a cancer-specific antigen generated by incorporating the cancer-specific antigen from outside the cell and degrating it in the cell, and it is expressed on the surface of the cell. A helper T cell, which has recognized the peptides bound to HLA class II molecule, is activated to generate various cytokines that activate other immunocompetent cells, so as to induce or reinforce an immune reaction against a tumor.

Thus, if an immunotherapy targeting an antigen specifically expressing at a high level in such a cancer can be developed, it can provide a therapeutic method effectively eliminating the cancer alone, without impairing normal autologous organs. Moreover, it is anticipated that such an immunotherapy can provide a therapeutic method applicable to patients suffering from a terminal-stage cancer, for whom no other treatments can be implemented. Furthermore, if a cancer-specific antigen and peptide are administered in the form of a vaccine to a human having a high risk of developing such a cancer, there is a possibility that the onset of the cancer can be prevented.

First, the present inventors have performed a genome-wide gene expression analysis. They have analyzed 23,040 types of genes in stomach cancer tissues and normal tissues utilizing a cDNA microarray. As a result, in 11 out of 20 cases of patients with diffuse infiltrative stomach cancer, the inventors have identified Secreted protein acidic and rich in cysteine (SPARC), which is a gene highly expressed in stomach cancer tissues, and the expression level of which is 5 or more times higher than that of normal tissues (130,000 times higher on average) (FIG. 1). The SPARC gene is expressed at a low level also in normal adipose tissues, mammary gland, ovary, spinal cord, testis, uterus, placenta, etc. However, the expression level of the SPARC gene in any of the aforementioned organs is lower than that of normal gastric mucous membrane by a factor of 5 times or less (FIG. 2).

Other researchers had already reported that SPARC is not only highly expressed in diffuse infiltrative stomach cancer but it is also expressed in pancreatic cancer and melanoma. Moreover, the present inventors have found that SPARC is secreted in the serum of melanoma patients, and that SPARC can be a useful tumor marker particularly for the early detection of melanoma (Japanese Patent Application No. 2004-303688; and Clinical Cancer Research 11: 8079-8088, 2005).

SPARC is a 43-KD acidic secretory protein consisting of 286 amino acids. This protein is rich in cysteine, and it moves to the nucleus during the cell division phase. In addition, SPARC controls the interaction between an extracellular matrix protein and a cell, so that it can be also associated with the control of cell growth. Since SPARC is expressed in osteoblasts, thrombocytes, and wound areas, it is considered that this protein is associated with the repair and reconstruction of tissues. Furthermore, it has also reported that SPARC is highly expressed also in cancers such as melanoma or osteosarcoma and in the interstitial cells of tumors, and that the expression of SPARC correlates with the prognosis, infiltration or metastasis of tumors.

[Non-Patent Document 1] Ikuta Y et al., Clinical Cancer Research 11: 8079-8088, 2005.
[Patent Document 1] Japanese Patent Application No. 2004-303688

DISCLOSURE OF THE INVENTION

Problems to be Solved by the Invention

It is an objective of the present invention to develop a method for enhancing the immunity of a patient suffering from metastatic cancer or intractable cancer, to which surgical therapy, chemotherapy and radiotherapy are used as treatments for tumors highly expressing SPARC, such as diffuse infiltrative stomach cancer, pancreatic cancer or melanoma, can hardly be applied, so as to alleviate the symptoms of such cancers and so as to carry out an immunotherapy suppressing the growth of such cancers. That is to say, it is an objective of the present invention to identify a peptide derived from an SPARC protein that is overexpressed in cancer tissue, which is able to induce a strong immune response to the aforementioned cancers without causing harmful phenomenon to cancer patients, and to apply the identified peptide to a tumor immunotherapy. That is, it is an objective of the present invention to identify a SPARC protein-derived peptide that is able to induce human killer T cells and helper T cells having reactivity to tumors, and to provide a means for carrying out a tumor immunotherapy on patients with various types of cancers highly expressing SPARC.

Means for Solving the Problems

The present inventors have identified a gene, SPARC, that is highly expressed in diffuse infiltrative stomach cancer, by performing cDNA microarray analysis on the aforementioned stomach cancer and various normal tissues. The expression of SPARC is observed also in several types of normal tissues. However, the expression level of SPARC in normal tissues is significantly lower than that in cancerous tissues. In order to examine the presence or absence of the induction of antitumor immunity by SPARC-specific killer T cells, there were utilized BALB/c mice that express mouse $K^d$ molecules, the characteristics of the amino acid sequence of the bound peptide of which are identical to those of HLA-A24 that is the most frequent HLA class I allele in the Japanese population. Human SPARC has 95% homologous amino acid sequence in comparison to mouse SPARC. Thereby peptides consisting of amino acid sequences shared between the humans and the mice, and having a binding motif shared by human HLA-A24 and mouse $K^d$, were synthesized. Thereafter, BALB/c mice ($K^d$-expressed) were immunized with bone marrow-derived dendritic cells, on which such a peptide mixture had been loaded, and the inventors investigated whether killer T cells reactive to SPARC-expressing cancer cells are induced or not. Moreover, with regard to mice that had been pre-treated by the same immunization method as described above, the inventors investigated whether the growth of the transplanted cancer cells expressing mouse SPARC is suppressed and the survival time of the mice is prolonged or not. Furthermore, whether or not a harmful phenomenon appears together with the occurrence of an autoimmune phenomenon in the peptide-immunized mice was also examined. As a result, it was found that the peptide having the amino acid sequence as shown in any one of SEQ ID NOS: 1 to 3 is able to induce killer T cells that destroy cancer cells expressing SPARC. Furthermore, the growth of the transplanted mouse cancer cells expressing SPARC is suppressed in mice immunized with the aforementioned peptide and thus the survival time of the mice is prolonged. The present invention has been completed based on these findings.

The present invention provides the following invention.
(1) A peptide of any of the following:
(A) a peptide which consists of the amino acid sequence as shown in any one of SEQ ID NOS: 1 to 3; or
(B) a peptide which consists of an amino acid sequence comprising a substitution or addition of one or several amino acids with respect to the peptide consisting of the amino acid sequence as shown in any one of SEQ ID NOS: 1 to 3, and which has ability to induce cytotoxic (killer) T cells.
(2) An immune inducing agent for cancers, which comprises at least one type of the peptide of (1).
(3) A medicament for treating and/or preventing tumors, which comprises at least one type of the peptide of (1).
(4) An agent for inducing antigen-presenting cells having high ability to induce tumor-reactive T cells, which comprises at least one type of the peptide of (1).
(5) An agent for inducing tumor-reactive T cells, which comprises at least one type of the peptide of (1).
(6) An agent for inducing antigen-presenting cells having high ability to induce tumor-reactive T cells, which comprises a gene encoding for a peptide of any of the following:
(A) a peptide which consists of the amino acid sequence as shown in any one of SEQ ID NOS: 1 to 3; or
(B) a peptide which consists of an amino acid sequence comprising a substitution or addition of one or several amino acids with respect to the peptide consisting of the amino acid sequence as shown in any one of SEQ ID NOS: 1 to 3, and which has ability to induce killer T cells.
(7) An antibody against the peptide of (1).
(8) A killer T cell, a helper T cell, or an immunocyte population comprising such cells, which is induced using the peptide of (1).
(9) An antigen-presenting cell, which presents a complex of an HLA molecule and the peptide of (1).
(10) The antigen-presenting cell of (9), which is induced using the agent of (4) or (6).

BEST MODE FOR CARRYING OUT THE INVENTION (1) Peptide of the Present Invention, and Immune Inducing Agent for Cancers Comprising the Same The peptide of the present invention is described in the following:
(A) a peptide which consists of the amino acid sequence as shown in any one of SEQ ID NOS: 1 to 3; or
(B) a peptide which consists of an amino acid sequence comprising a substitution or addition of one or several amino acids with respect to the amino acid sequence as shown in any one of SEQ ID NOS: 1 to 3, and which has ability to induce killer T cells.

The term "peptide having ability to induce cytotoxic T cells" is used in the present specification to mean a peptide having a activity to stimulate tumor-reactive killer T cells.

A method for obtaining/producing the peptide of the present invention is not particularly limited. Either a chemically synthesized peptide, or a recombinant peptide produced by genetic recombination, may be used.

When a chemically synthesized peptide is obtained, the peptide of the present invention can be synthesized by a chemical synthesis method such as an Fmoc method (fluorenylmethyloxycarbonyl method) or a tBoc method (t-butyloxycarbonyl method), for example. In addition, the peptide of the present invention can also be synthesized using various types of commercially available peptide synthesizers.

When the peptide of the present invention is produced in the form of a recombinant protein, DNA having a nucleotide sequence encoding the aforementioned peptide, a mutant thereof, or a homologue thereof is obtained, and it is then introduced into a preferred expression system, so as to produce the peptide of the present invention.

As an expression vector, a vector capable of autonomously replicating in a host cell or capable of being incorporated into the chromosome of a host cell may preferably be used. An expression vector comprising a promoter at a position capable of expressing a gene encoding for the peptide is used. In addition, a transformant having a gene encoding for the peptide of the present invention can be produced by introducing the aforementioned expression vector into a host. As a host, any one of a bacterium, yeast, an animal cell, and an insect cell may be used. An expression vector may be introduced into a host according to a known method, depending on the type of such a host.

In the present invention, the transformant as produced above is cultured, and the peptide of the present invention is then generated and accumulated in a culture. Thereafter, the peptide of the present invention is collected from the culture, so as to isolate a recombinant peptide.

When such a transformant is a prokaryote such as *Escherichia coli* or a eukaryote such as yeast, a medium used for culturing such microorganisms may be either a natural medium or a synthetic medium, as long as it contains a carbon source, a nitrogen source, inorganic salts, and the like that can be assimilated by the aforementioned microorganisms, and it is able to efficiently carry out the culture of the transformant. Moreover, such culture may be carried out under conditions that are commonly applied for culturing the aforementioned microorganisms. After completion of the culture, the peptide of the present invention may be isolated and purified from the culture of the transformant according to a common method of isolating and purifying a peptide.

The term "one or several amino acids" is used in the present specification to mean generally 1 to 10 amino acids, preferably 1 to 8 amino acids, more preferably 1 to 5 amino acids, and particularly preferably 1 to 3 amino acids (for example, 1, 2 or 3 amino acids).

A peptide consisting of an amino acid sequence comprising a substitution or addition of one or several amino acids with respect to the peptide consisting of the amino acid sequence as shown in any one of SEQ ID NOS: 1 to 3 can be appropriately produced or acquired by persons skilled in the art based on information regarding the amino acid sequence as shown in any one of SEQ ID NOS: 1 to 3. That is to say, a peptide which consists of an amino acid sequence comprising a substitution or addition of one or several amino acids with respect to the amino acid sequence as shown in any one of SEQ ID NOS: 1 to 3 and which has ability to induce cytotoxic T cells, can be produced by any given method known to persons skilled in the art, such as the aforementioned chemical synthesis, genetic engineering means, or mutagenesis. For example, site-directed mutagenesis which is a genetic engineering means is useful because it is a means for introducing a specific mutation into a specific position. Such site-directed mutagenesis can be carried out by a method described in Molecular Cloning: A laboratory Manual, $2^{nd}$ Ed., Cold Spring Harbor Laboratory, Cold Spring Harbor, N.Y., 1989 (hereinafter abbreviated as Molecular Cloning $2^{nd}$ Ed.), Current Protocols in Molecular Biology, Supplement 1 to 38, John Wiley & Sons (1987-1997) (hereinafter abbreviated as Current Protocols in Molecular Biology), etc.

As described later in examples, the aforementioned peptide of the present invention is able to induce immunity against cancers. Thus, the present invention provides an immune inducing agent for cancers, which comprises the peptide of the present invention.

The immune inducing agent of the present invention used for cancers is used in vitro, ex vivo, or in vivo, and preferably ex vivo, so that it can induce killer T cells, helper T cells, or an immunocyte population comprising such cells, thereby imparting immunity against cancers.

(2) Antibody of the Present Invention

The present invention also relates to an antibody that recognizes a part or whole of the aforementioned peptide of the present invention as an epitope (antigen), and a killer T cell induced by ex vivo or in vitro stimulation using the aforementioned peptide. In general, it has been known that such a killer T cell exhibits an antitumor activity that is stronger than that of an antibody.

The antibody of the present invention may be either a polyclonal antibody or a monoclonal antibody. Such an antibody can be produced by a common method.

For example, a polyclonal antibody can be produced by immunizing a mammal or Ayes with the peptide of the present invention used as antigen, then collecting blood from the mammal or Ayes, and then separating and purifying an antibody from the collected blood. For example, mammals or Ayes, such as a mouse, a hamster, a guinea pig, a chicken, a rat, a rabbit, a canine, a goat, a sheep, a bovine or a horse, can be immunized. Such an immunization method is known to persons skilled in the art. For example, an antigen may be administered 2 or 3 times at intervals of 7 to 30 days. As a dosage, approximately 0.05 to 2 mg of antigen can be administered once, for example. An administration route is not particularly limited, and subcutaneous administration, intracutaneous administration, intraperitoneal administration, intravenous administration, intramuscular administration, etc. can be selected, as appropriate. Moreover, an antigen can be dissolved in a suitable buffer containing an adjuvant, for example, in a suitable buffer containing a commonly used adjuvant such as a complete Freund's adjuvant or aluminum hydroxide, and it can be used.

Thus the immunized mammal or Aves is bred for a certain period of time. Thereafter, if the antibody titer increases, a booster can be carried out using 100 to 1,000 µg of antigen, for example. One or two months after the final immunization, blood is collected from the immunized mammal or Ayes. The thus collected blood (polyclonal antiserum) is then separated and purified by an ordinary method including centrifugation, precipitation using ammonium sulfate or polyethylene glycol, chromatography such as gel filtration chromatography, ion exchange chromatography, or affinity chromatography, etc., so as to obtain a polyclonal antibody that recognizes the peptide of the present invention.

On the other hand, a monoclonal antibody can be obtained by preparing a hybridoma. For example, such a hybridoma can be obtained by cell fusion of an antibody-generating cell and a myeloma cell. A hybridoma that generates the monoclonal antibody of the present invention can be obtained by the following cell fusion method.

As an antibody-generating cell, a spleen cell, a lymph node cell, a B lymphocyte, or the like obtained from the immunized animal is used. As an antigen, the peptide of the present invention is used. As an animal to be immunized, a mouse, a rat, or the like can be used. An antigen is administered to such an animal according to an ordinary method. For example, a suspension or emulsified liquid comprising an adjuvant such as a complete Freund's adjuvant or incomplete Freund's adjuvant and the peptide of the present invention used as an antigen is administered to an animal via intravenous administration, subcutaneous administration, intracutaneous administration, intraperitoneal administration, etc., several times, so as to immunize the animal. Thereafter, an antibody-generating cell such as a spleen cell is obtained from the immunized animal, and the thus obtained spleen cell is then fused with a myeloma cell according to a known method (G. Kohler et al., Nature, 256 495 (1975)), thereby producing a hybridoma.

Examples of a myeloma cell strain used in cell fusion include a P3X63Ag8 strain, a P3U1 strain and an Sp2/0 strain, in the case of a mouse. When such cell fusion is carried out, a fusion promoter such as polyethylene glycol or Sendai virus is used. For selection of a hybridoma after completion of the cell fusion, a hypoxanthine aminopterin thymidine (HAT) medium is used according to an ordinary method. The hybridoma obtained as a result of the cell fusion is cloned by a limiting dilution method. Further, as necessary, screening is carried out by an enzyme immunoassay using the peptide of the present invention, so as to obtain a cell strain that generates a monoclonal antibody specifically recognizing the peptide of the present invention.

In order to produce a monoclonal antibody of interest from the thus obtained hybridoma, the hybridoma may be cultured by a common cell culture method or ascites formation method, and the monoclonal antibody of interest may be then purified from the culture supernatant or ascites. The monoclonal antibody may be purified from the culture supernatant or ascites according to an ordinary method. For example, ammonium sulfate fractionation, gel filtration, ion exchange chromatography, affinity chromatography, and other methods may be combined as appropriate and used.

Moreover, the fragments of the aforementioned antibody are also included in the scope of the present invention. Examples of such an antibody fragment include an F(ab')2 fragment and an Fab' fragment.

(3) Killer T Cell, Helper T Cell, or Immunocyte Population Comprising Such Cells The present invention also relates to a killer T cell, a helper T cell or an immunocyte population comprising such cells, which is induced by in vitro stimulation using the peptide of the present invention. For example, when peripheral blood lymphocytes or tumor-infiltrating lymphocytes are stimulated in vitro with the peptide of the present invention, activated T cells exhibiting tumor-reactivity are induced. Thus the activated T cells can be effectively used for an adoptive immunotherapy of cancer. Furthermore, the peptide of the present invention is allowed to be expressed in dendritic cells that are strong antigen-presenting cells in vivo or in vitro, and dendritic cells expressing the antigenic peptide are then administered so as to induce an immune response to tumors.

Preferably, a killer T cell, a helper T cell, or an immunocyte population comprising such cells can be induced by ex vivo or in vitro stimulation using the peptide of the present invention and an immunostimulator. Examples of such an immunostimulator used herein include a cell growth factor and a cytokine.

The thus obtained killer T cell, helper T cell, or immunocyte population comprising such cells is transferred into a body, so that tumor can be suppressed and that cancer can be prevented and/or treated.

Further, using the peptide of the present invention, a killer T cell, a helper T cell, or an immunocyte population comprising such cells, which is capable of suppressing tumor growth as described above, can be produced. Accordingly, the present invention provides a cell culture solution comprising tumor-reactive T cells and the peptide of the present invention. Using such a cell culture solution, a killer T cell, a helper T cell, or an immunocyte population comprising such cells, which is capable of suppressing tumor growth, can be produced. Still further, the present invention also provides a cell culture kit for producing a killer T cell, a helper T cell, or an immunocyte population comprising such cells, which comprises the aforementioned cell culture solution and a cell culture vessel.

(4) Medicament of the Present Invention for Treating and/or Preventing Tumor (Cancer Vaccine)

Since the peptide of the present invention is able to induce cancer cell-specific killer T cells, it can be expected as an agent for treating and/or preventing cancer. For example, bacteria such as BCG (Bacillus Calmette-GuErin) which was transformed with recombinant DNA produced by incorporating a gene encoding for the peptide of the present invention into a suitable vector, or viruses such as vaccinia virus, into the genome of which DNA encoding for the peptide of the present invention has been incorporated, can be effectively used as a live vaccine for treating and/or preventing human cancers. It is to be noted that the dosage and administration method of a cancer vaccine are the same as those in the case of an ordinary smallpox vaccination or BCG vaccination.

That is to say, DNA encoding for the peptide of the present invention (which is used as is, or is in the form of plasmid DNA incorporated into an expression vector), or a recombinant virus or recombinant bacteria comprising the aforementioned DNA, can be administered as a cancer vaccine to mammals including a human, directly or in a state where it is dispersed in an adjuvant. Likewise, the peptide of the present invention can also be administered as a cancer vaccine in a state where it is dispersed in an adjuvant.

Examples of an adjuvant used in the present invention include an incomplete Freund's adjuvant, BCG, trehalose dimycolate (TDM), lipopolysaccharide (LPS), an alum adjuvant, and a silica adjuvant. From the viewpoint of ability to induce antibody, an incomplete Freund's adjuvant (IFA) is preferably used.

The type of a cancer is not particularly in the present specification. Specific examples of a cancer include stomach cancer, colon cancer, esophageal cancer, pancreatic cancer, hepatic cancer, gallbladder cancer, cholangiocarcinoma, lung cancer, breast cancer, thyroid cancer, melanoma (malignant melanoma), skin cancer, osteosarcoma, pheochromocytoma, head and neck cancer, brain tumor, chronic myelogenous leukemia, acute myelogenous leukemia, malignant lymphoma, kidney cancer, bladder cancer, prostatic cancer, testicular cancer, uterine cancer, ovarian cancer, and soft tissue sarcoma. Of these, cancers that highly express SPARC, such as stomach cancer (in particular, diffuse infiltrative stomach cancer), pancreatic cancer, and melanoma (malignant melanoma), are typical examples.

The peptide of the present invention acts as a T cell epitope to induce a cancer cell-specific killer T cell or helper T cell. Thus, the peptide of the present invention is useful as an agent for preventing and/or treating human cancers. In addition, if the antibody of the present invention is able to inhibit the activity of SPARC as a cancer antigen, it is also useful as an agent for preventing and/or treating human cancers. As an actual usage, the peptide or antibody of the present invention can be administered as an injection product, directly or together with a pharmaceutically acceptable carrier and/or diluent, and as necessary, also together with the below-mentioned auxiliary substances. Moreover, the peptide or antibody of the present invention can also be administered by a method such as spraying, via transdermal absorption through mucosa. The term "carrier" is used herein to mean human serum albumin, for example.

In addition, as a diluent, PBS, distilled water, or the like can be used.

As a dosage, the peptide or antibody of the present invention can be administered within the range between 0.01 and 100 mg per adult per administration. However, the dosage is not limited to the aforementioned range. The dosage form is not particularly limited, either. A freeze-dried product, or a granule produced by adding an excipient such as sugar, may also be available.

Examples of an auxiliary substance, which may be added to the agent of the present invention to enhance tumor-reactive T cell-inducing activity, include: muramyl-dipeptide (MDP); bacterial components such as BCG bacteria; ISCOM described in Nature, vol. 344, p. 873 (1990); saponin QS-21 described in J. Immunol. vol. 148, p. 1438 (1992); liposome; and aluminum oxide. Further, immunostimulators such as lenthinan, schizophyllan, or Picibanil may also be used as auxiliary substances. Other examples of products used herein as auxiliary substances include: cytokines for enhancing the growth or differentiation of T cells, such as IL-2, IL-4, IL-12, IL-1, IL-6, or TNF; α galactosylceramide for activating NKT cells; CpG that binds to a Toll-like receptor to activate a natural immune system; and lipopolysaccharide (LPS).

Furthermore, the aforementioned antigen peptide is added in vitro to cells collected from a HLA-A24-positive patient or allogeneic cells isolated from anyone else who is HLA-A24-positive, followed by antigen presentation of the cells. Thereafter, the cells are administered into the blood vessel of the patient, so that killer T cells can be effectively induced in the body of the patient. Further, the present peptide is added to the peripheral blood lymphocytes of a patient, and the obtained mixture is then cultured in vitro. Thereby, killer T cells can be induced in vitro, and they can be then returned to the blood vessel of the patient. Such a therapy involving cell transfer has already been carried out as a method for treating cancers, and thus it is a method well known to persons skilled in the art.

By introducing the peptide of the present invention into a body, tumor-reactive T cells are induced, and as a result, an antitumor effect can be anticipated. Moreover, when lymphocytes are stimulated by the peptide of the present invention ex vivo or in vitro, activated T cells are induced. The activated T cells are injected into an affected area. Thus, this technique can be effectively used for an adoptive immunotherapy.

The present invention will be further described in the following examples. However, these examples are not intended to limit the scope of the present invention.

EXAMPLES

Example 1

(1) cDNA Microarray Analysis

With regard to the excised cancerous tissue of a patient with diffuse infiltrative stomach cancer, a cancerous tissue was distinguished from non-cancerous tissues by Laser capture microdissection, and both the cancerous and non-cancerous portions were then cut out. Thereafter, RNA was extracted from each tissue. When cDNA was synthesized from such RNA by a reverse transcription reaction, cDNA generated from cancerous tissue was fluorescently labeled with Cy5, and cDNA generated from non-cancerous tissue was fluorescently labeled with Cy3. Subsequently, the two cDNA preparations were mixed to obtain target DNA. Hybridization was carried out on a slide glass on which probe cDNA had been arrayed, and non-specific bonds were then eliminated by washing. Thereafter, fluorescence images obtained after the hybridization were captured using a CCD camera or a fluorescence scanner, and they were then displayed with false colors (Cy5: red; Cy3: green). At the same time, the ratio of the two types of fluorescence intensity (R/G) was calculated, and it was indicated as a gene expression profile. Moreover, the expression of 23,040 types of genes in the cancerous and non-cancerous portions of 20 patients with diffuse infiltrative stomach cancer was subjected to comparative investigation, and 15 types of genes of which expression ratio in cancerous tissue/non-cancerous tissue was 5 or greater were selected (FIG. 1).

Subsequently, the expression profile of the 23,040 types of genes in the normal tissues of 29 organs (including 4 embryonal organs) was analyzed, and genes of which expression level was low in such normal organs were selected. In the case of SPARC, which we selected as a tumor antigen in this experiment, the expression ratio of cancerous/non-cancerous portions was 5 or greater (133,359 times on average) in 11 out of 20 patients with diffuse infiltrative stomach cancer. SPARC was expressed in some normal tissues, but the expression levels in such a non-cancerous tissues were significantly lower than that in a cancerous tissues (FIG. 2).

Example 2

(2) Selection of Human HLA-A24- and Mouse $K^d$-Restricted SPARC Peptide Repertoires In human and mouse SPARC having a homology of 95%, the following peptides were selected from the fragment of SPARC of which amino acid sequences were shared between humans and mice. The total amino acid sequences of SPARC molecules were searched based on known information regarding amino acid sequences commonly observed in peptides having strong binding affinity to both human HLA-A24 and mouse $K^d$ molecules. The repertoires of peptides that were assumed to have high binding affinity for the two types of molecules were selected by using a computer program. As a result, 4 types of peptides were selected as candidate peptides (Table 1).

TABLE 1

SPARC-derived peptides possibly having binding affinity to both human HLA-A24 and mouse $K^d$ molecules

| Peptide | Sequence | Start position | Binding score A24 | $K^d$ |
|---|---|---|---|---|
| SPARC- $K^d$-1 | DYIGPCKYI | 143 | 75 | 400 |
| SPARC- $K^d$-2 | HFFATKCTL | 123 | 20 | 1382 |
| SPARC- $K^d$-3 | EFPLRMRDWL | 161 | 30 | 960 |
| SPARC- $K^d$-4 | MYIFPVHWQF | 225 | 210 | 120 |

Predicted by //bimas.dcrt.nih.gov/cgi-bin/molbio/ken parker comboform
SPARC Kd-1: SEQ ID NO: 1
SPARC Kd-3: SEQ ID NO: 2
SPARC Kd-4: SEQ ID NO: 3
SPARC Kd-2: SEQ ID NO: 4

(3) Dendritic Cell (DC) Vaccine

Bone marrow-derived dendritic cells (BM-DC) were induced from bone marrow cells derived from BALBc bone marrow by using GM-CSF as described previously by us (Nakatsura, T et al., Clin Cancer Res 10, 8630-8640, 2004). Thus the obtained BM-DC were cultured with a mixture of the 4 types of peptides selected as described above at a concentration of 10 µM for 2 hours, and the peptide-pulsed BM-DC (5×10⁵ cells) were then intraperitoneally administered to each mouse. After an interval of 1 week, the same peptide-pulsed BM-DC were administered to the mouse twice, so that the mouse was strongly immunized. Thereafter, the spleen cells of the mouse were recovered and induction of killer T cells was evaluated. In order to strictly analyze induction of killer T cells derived from CD8⁺ T cells, after collection of the spleen, CD4+ T cells were eliminated from the collected spleen cells, using MACS beads, and the remaining cells were then used for analysis.

The following protocols were used for generation and characterization of SPARC-specific killer T cells (The day of recovering the spleen cells from the immunized mouse was defined as Day 0.)

Day −21 (1) GM-CSF was added to the bone marrow cells of a BALB/c mouse, so as to start induction of bone marrow-derived dendritic cells (hereinafter referred to as BM-DC).

Day −14 (2) A mixture of the 4 types of SPARC peptides was added to the induced BM-DC, and 2 hours later, $5 \times 10^5$ cells were intraperitoneally administered to each mouse.

Steps (1) and (2) were repeated twice every other week.

Day 0 The spleen cells of the immunized BALB/c mouse were recovered. The cells were co-cultured with BM-DC prepulsed with each SPARC peptide for 2 hours. Thereafter, the resultant cells was co-cultured for 6 days.

Day 6 In order to detect killer T cells specifically recognizing the SPARC peptides, a Cr-release assay was carried out. T2K$^d$ cells, an RL male 1 cell line, a Meth A cell line, and a BALB/3T3 cell line were selected as target tumor cells for killer T cells.

(4) Analysis of Cytotoxic Effects of SPARC-Specific Killer T Cells on Tumor Cells by Cr-Release Assay The cytotoxic activity of the induced SPARC-specific killer T cells on tumor cells was analyzed as follows. T2K$^d$ cell is a cell line obtained by introducing a K$^d$ gene into a mouse T2 cell line that lacks the expression of a TAP gene. Only in a case when a peptide added from outside binds to an MHC class I molecule due to TAP deficiency, the expression of a complex of the MHC class I molecule and the peptide is stably expressed on the cell surface. An RL male 1 cell line is BALB-c mouse-derived T-cell leukemic cells and does not express SPARC. The above two types of cells do not express SPARC. On the other hand, a Meth A cell line and a BALB/3T3 cell line are BALB/c mouse-derived fibrosarcoma cell line and fibroblast cell line, respectively. Both of these cell lines express SPARC. The aforementioned cell lines were labeled with radioactive chromium (Cr), and they were then cultured with the aforementioned killer T cells for 4 hours. Thereafter, a culture supernatant was recovered, and the amount of radioactive Cr released from dead cells was quantified, so that cytotoxic activity was detected.

As a result, no cytotoxicity to T2K$^d$ cells and RL male 1 cells, which did not express SPARC, was observed. However, cytotoxicity was observed specifically to the T2K$^d$ cells, which expressed a SPARC peptides in the context of the K$^d$ molecule on the surface by loading the SPARC K$^d$ peptides 1, 3 and 4, and also to Meth A and BALB/3T3, which spontaneously expressed SPARC (FIG. 3).

Example 3

(5) Induction of Antitumor Immunity in BALB/c Mice by Immunization with SPARC Peptide (Method)

BM-DC was cultured with a mixture of SPARC K$^d$-1, 3 and 4 peptides (10 μM for each) for 2 hours. Thereafter, $5 \times 10^5$ cells were intraperitoneally administered to each mouse. After an interval of 1 week, a peptide-loaded BM-DC was administered to the mouse in the same manner, so that the mouse was immunized two times in total. Seven days later, a mouse fibrosarcoma cell line, Meth A ($1 \times 10^6$ cells), which highly express mouse SPARC, was subcutaneously transplanted to the mouse. Thus, the growth of the tumor and the survival time of the mouse were examined.

(Results)

The results are shown in FIG. 4. Preventive administration of SPARC peptide pulsed BM-DC could induced inhibition of the growth of the subcutaneously transplanted Meth A and induced a prolongation of the survival time of the mouse.

INDUSTRIAL APPLICABILITY

HLA-A24 (A*2402) is the most frequent HLA class I allele, possessed by approximately 60% of the Japanese. The structural motifs of peptides bound to the K$^d$ molecules of BALB/c mouse is significantly similar to those of peptides bound to the human HLA-A24 molecules. Accordingly, it was revealed that, when a BALB/c mouse is immunized with a certain peptide, if the peptide binds to the K$^d$ molecule and thereby induces killer T cells, and if the killer T cells destroy cancer cells that express a complex of the peptide and the K$^d$ molecule, it is highly possible that the peptide also binds to HLA-A24 and induces human killer T cells that can destroy cancer cells. Therefore, the peptide of the present invention can be applicable to an immunotherapy for patients with diffuse infiltrative stomach cancer, pancreatic cancer and melanoma, who possess HLA-A24. It is anticipated that the QOL of the patients can be improved by suppressing the growth or progression of such cancers by SPARC peptide-based cancer immunotherapy.

SEQUENCE LISTING

Figure 1:
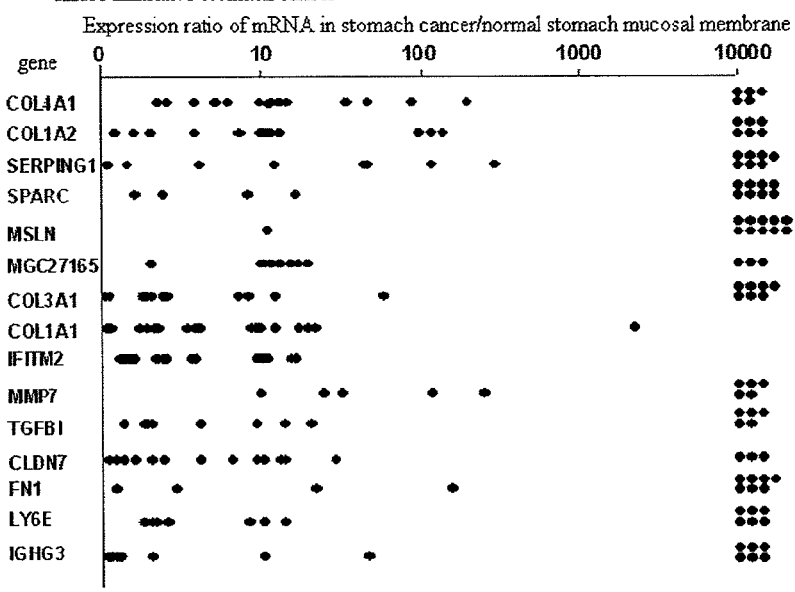
FIG. 1 shows the degree of expression of the top 15 genes that were expressed in stomach cancer tissues at a level higher than in normal stomach mucosal membrane, which were identified by performing cDNA microarray analysis on 20 patients with diffuse infiltrative stomach cancer. Taking into consideration the obtained results as well as the results of the cDNA microarray analysis of normal tissues as described below, from the aforementioned 15 genes, secreted protein acidic and rich in cysteine (SPARC) specifically overexpressed in a cancerous tissue was selected as the most ideal cancer-specific antigen in diffuse infiltrative stomach cancer.
Figure 2:
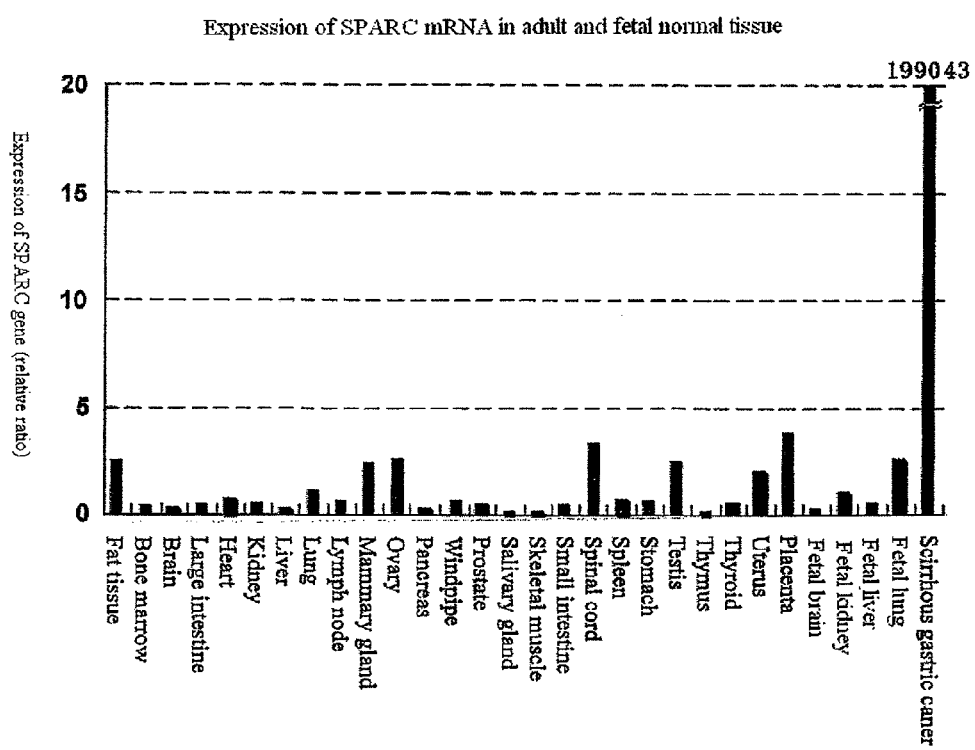
FIG. 2 shows the results obtained by analyzing the expression of SPARC in 25 types of main adult organs and in 4 types of embryonal organs, using a cDNA microarray. The expression of the SPARC gene was observed even in some normal tissues, but the expression level in such normal tissues was significantly lower than that in a cancerous tissue.
Figure 3:
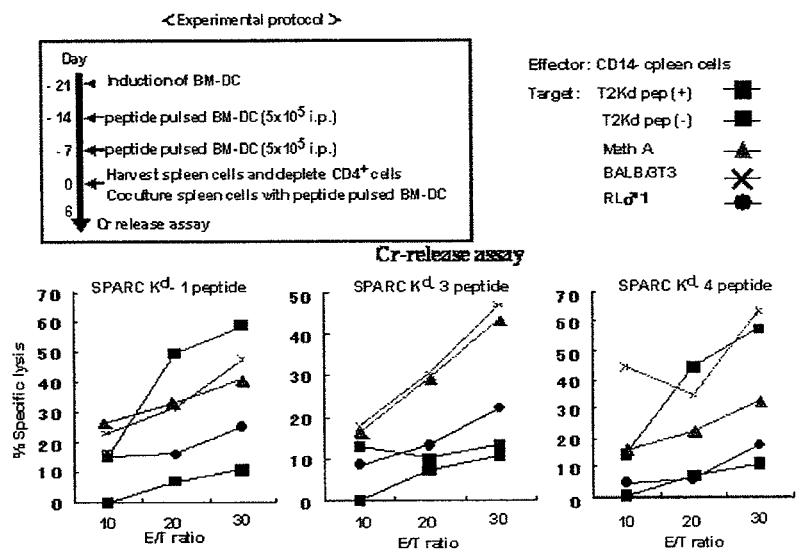
FIG. 3 shows the cytotoxicity of SPARC-positive tumor cells by CTL which was induced using a mouse K$^d$-restricted SPARC K$^d$-1, K$^d$-3 or K$^d$-4 epitope peptide in BALB/c mice.
Figure 4:
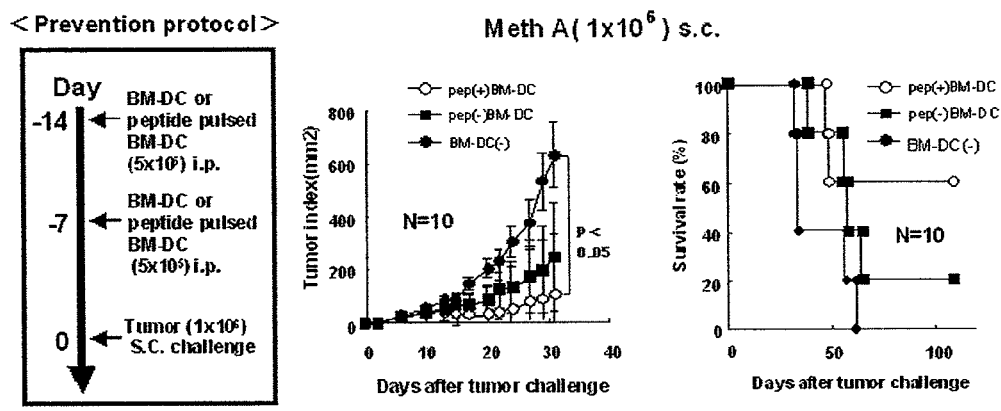
FIG. 4 shows the suppression of the growth of the subcutaneously transplanted Meth A cancer cells and the extension of the survival time of BALB/c mice by pre-administration of bone marrow-derived dendritic cells (BM-DC) loaded with a mixture of SPARC K$^d$-1, K$^d$-3 and K$^d$-4 peptides.

```
<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Tyr Ile Gly Pro Cys Lys Tyr Ile
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Phe Pro Leu Arg Met Arg Asp Trp Leu
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Tyr Ile Phe Pro Val His Trp Gln Phe
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Phe Phe Ala Thr Lys Cys Thr Leu
1               5
```

What is claimed is:

1. An isolated peptide of any of the following:
   (A) a peptide which consists of the amino acid sequence as shown in SEQ ID NO: 2; or
   (B) a peptide which consists of the amino acid sequence comprising a substitution or addition of one to three amino acids with respect to the peptide consisting of the amino acid sequence as shown in SEQ ID NO: 2, and which has capacity to induce cytotoxic (killer) T cells.

2. A composition which comprises at least one type of the peptide of claim 1.

3. An isolated antigen-presenting cell, which comprises a complex of an HLA molecule and the peptide of claim 1.

* * * * *